(12) United States Patent
Han

(10) Patent No.: US 11,678,818 B2
(45) Date of Patent: Jun. 20, 2023

(54) BLOOD GLUCOSE DETECTION DEVICE AND METHOD OF DETERMINING BLOOD GLUCOSE LEVEL

(71) Applicant: BOE TECHNOLOGY GROUP CO., LTD., Beijing (CN)

(72) Inventor: Litong Han, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 769 days.

(21) Appl. No.: 16/332,477

(22) PCT Filed: Jul. 19, 2018

(86) PCT No.: PCT/CN2018/096237
§ 371 (c)(1),
(2) Date: Mar. 12, 2019

(87) PCT Pub. No.: WO2019/114270
PCT Pub. Date: Jun. 20, 2019

(65) Prior Publication Data
US 2021/0212604 A1      Jul. 15, 2021

(30) Foreign Application Priority Data

Dec. 15, 2017   (CN) .......................... 201711349086.9

(51) Int. Cl.
*A61B 5/1455* (2006.01)
*A61B 5/145* (2006.01)
*A61B 5/00* (2006.01)

(52) U.S. Cl.
CPC ........ *A61B 5/14532* (2013.01); *A61B 5/1455* (2013.01); *A61B 5/6838* (2013.01);
(Continued)

(58) Field of Classification Search
CPC .............. A61B 5/1455; A61B 5/14552; A61B 5/14532; A61B 5/6838; A61B 5/7225; A61B 5/7278; A61B 2562/0238
See application file for complete search history.

(56) References Cited

U.S. PATENT DOCUMENTS 5,830,132 A * 11/1998 Robinson ............. A61B 5/1455
                                                        600/316
6,064,898 A *  5/2000 Aldrich .............. A61B 5/14532
                                                        600/323
(Continued)

FOREIGN PATENT DOCUMENTS

CN       1642478 A       7/2005
CN       1653324 A       8/2005
(Continued)

OTHER PUBLICATIONS

Search Report and Written Opinion, dated Nov. 1, 2018, issued in counterpart International Application No. PCT/CN2018/096237 (11 pages; in English).
(Continued)

*Primary Examiner* — Eric F Winakur
(74) *Attorney, Agent, or Firm* — WHDA, LLP

(57) ABSTRACT

The present disclosure generally relates to the field of blood glucose monitoring. A device for determining a blood glucose level includes a first light emitting unit configured to emit a first light; a second light emitting unit configured to emit a second light, wherein one of the first light and the second light is configured to be insensitive to glucose content in blood; a first light receiving unit configured to generate a first signal based on the first light; and a second light receiving unit configured to generate a second signal based on the second light.

15 Claims, 7 Drawing Sheets

(52) U.S. Cl.
CPC .......... *A61B 5/7225* (2013.01); *A61B 5/7278* (2013.01); *A61B 5/6826* (2013.01); *A61B 2562/0238* (2013.01)

(56) References Cited

U.S. PATENT DOCUMENTS

| | | | |
|---|---|---|---|
| 6,149,588 A | 11/2000 | Noda et al. | |
| 7,486,976 B1 * | 2/2009 | Belotserkovsky | A61B 5/14532 600/310 |
| 9,642,568 B2 | 5/2017 | Shah et al. | |
| 2005/0171415 A1 | 8/2005 | Hirao | |
| 2006/0063983 A1 | 3/2006 | Yamakoshi | |
| 2008/0027297 A1 | 1/2008 | Yamakoshi | |
| 2008/0312886 A1 | 12/2008 | Kyriacou et al. | |
| 2011/0131021 A1 * | 6/2011 | Xu | G01N 21/359 703/2 |
| 2014/0350364 A1 | 11/2014 | Markle et al. | |
| 2015/0276589 A1 | 10/2015 | Wagner et al. | |
| 2016/0095533 A1 | 4/2016 | Shang | |
| 2016/0157733 A1 | 6/2016 | Gil | |
| 2018/0146893 A1 | 5/2018 | Kryzhanovskii et al. | |

FOREIGN PATENT DOCUMENTS

| | | |
|---|---|---|
| CN | 103349553 A | 10/2013 |
| CN | 103917858 A | 7/2014 |
| CN | 106255461 A | 12/2016 |
| CN | 106793950 A | 5/2017 |
| CN | 107427263 A | 12/2017 |
| JP | H10-78437 A | 3/1998 |
| JP | 2000-258343 A | 9/2000 |

OTHER PUBLICATIONS

Office Action dated Dec. 25, 2019 issued in counterpart Chinese Application No. 201711349086.9 (w/ English machine translation; 22 pages).

* cited by examiner

BLOOD GLUCOSE DETECTION DEVICE AND METHOD OF DETERMINING BLOOD GLUCOSE LEVEL

CROSS-REFERENCE TO RELATED APPLICATIONS

This application claims the benefit of the filing date of Chinese Patent Application No. 201711349086.9 filed on Dec. 15, 2017, the entire disclosure of which is hereby incorporated by reference.

TECHNICAL FIELD

The present disclosure generally relates to the field of health monitoring, and in particular, to the monitoring of blood glucose. The present disclosure further relates to a blood glucose detection device and a method of determining blood glucose level.

BACKGROUND

Rapid advances have been made in the medical field to develop non-invasive technologies for measuring blood glucose. With the growing popularity of wearable devices (for example, a smart watch) equipped with heart rate monitoring functions comes an increase in the demand for the additional capability of blood glucose monitoring.

BRIEF SUMMARY

One embodiment of the present disclosure is a device for determining a blood glucose level. The device may comprise a first light emitting unit configured to emit a first light; a second light emitting unit configured to emit a second light, wherein one of the first light and the second light is configured to be insensitive to glucose content in blood; a first light receiving unit configured to generate a first signal based on the first light; and a second light receiving unit configured to generate a second signal based on the second light.

In some embodiments, one of the first light and second light may have a first wavelength in the range of 830 nm to 880 nm, and the other of the first light and second light may have a second wavelength in the range of 920 nm to 950 nm.

In some embodiments, the device may further comprise a difference circuit configured to receive the first signal and the second signal from the first light receiving unit and the second light receiving unit, respectively, and to calculate a difference value corresponding to the difference between the first signal and the second signal.

In some embodiments, the device may further comprise a storage unit configured to store a first correspondence table. The first correspondence table may comprise a plurality of difference values, a plurality of blood glucose concentrations, and a plurality of correspondence sets for each combination of corresponding difference value and blood glucose concentration.

In some embodiments, the device may further comprise a calculation unit configured to receive the calculated difference value from the difference circuit, and to determine the blood glucose level by identifying a correspondence set based on the calculated difference value and determining the corresponding blood glucose concentration according to the correspondence set.

In some embodiments, the device may further comprise an amplifier connected to the difference circuit, and configured to amplify the first signal and the second signal. The amplifier may comprise a first amplifier configured to receive and amplify the first signal and a second amplifier configured to receive and amplify the second signal.

In some embodiments, the difference circuit may comprise a third amplifier configured to amplify the difference between the first signal and the second signal.

In some embodiments, the first amplifier may be an inverting amplifier. The second amplifier may be a non-inverting amplifier. The third amplifier may be a differential amplifier.

In some embodiments, the storage unit may be further configured to store a second correspondence table, and the second correspondence table may comprise a plurality of body temperature values, a plurality of predetermined body temperature-dependent deviations in blood glucose concentration, and a plurality of correspondence sets for each combination of corresponding body temperature value and body temperature-dependent deviation in blood glucose concentration.

In some embodiments, the device may be further configured to determine a body temperature and to determine a correction value to be applied to the blood glucose level determination, by identifying a correspondence set based on the measured body temperature and determining the corresponding body temperature-dependent deviation in blood glucose concentration.

Another embodiment of the present disclosure is a wearable device for determining a blood glucose level. The wearable device may comprise a device as described above.

In some embodiments, the wearable device may be a clamp assembly comprising a first member and an opposing second member joined to one another by a pivotal connection. Each of the first light emitting unit and the second light emitting unit may be provided on one of the first member and the second member. Each of the first light receiving unit and the second light receiving unit may be provided on the other one of the first member and the second member, so that each of the first light receiving unit and the second light receiving unit may be directly opposite from the corresponding first light emitting unit and second light emitting unit.

Another embodiment of the present disclosure is a method of determining a blood glucose level. The method may comprise receiving a first light emitted by a first light emitting unit; receiving a second light emitted by a second light emitting unit, wherein one of the first light and the second light is configured to be insensitive to glucose content in blood; calculating a difference value corresponding to a difference between a first signal generated based on the first light and a second signal generated based on the second light; and determining the blood glucose level based on the calculated difference value.

In some embodiments, the method may further comprise amplifying the first signal and the second signal. The difference value may correspond to a difference between the amplified first signal and the amplified second signal.

In some embodiments, the method may further comprise measuring a body temperature; calculating a correction value corresponding to a deviation in the blood glucose level determination in accordance with the measured body temperature; and applying the correction value to the blood glucose level determination.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the present disclosure are apparent from the following detailed description taken in conjunction with the accompanying drawings in which:

Figure 1:
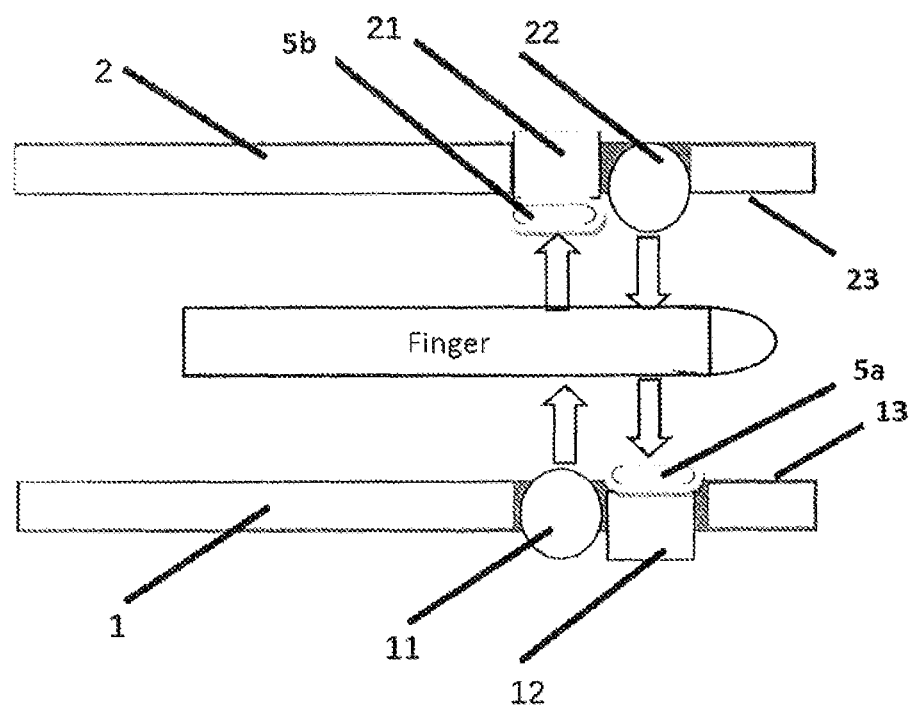
FIG. 1 shows a schematic diagram of a blood glucose detection device according to an embodiment of the present disclosure.

The various features of the drawings are not to scale as the illustrations are for clarity in facilitating one skilled in the art in understanding the invention in conjunction with the detailed description.

DETAILED DESCRIPTION

Next, the embodiments of the present disclosure will be described clearly and concretely in conjunction with the accompanying drawings, which are described briefly above. The subject matter of the present disclosure is described with specificity to meet statutory requirements. However, the description itself is not intended to limit the scope of this disclosure. Rather, the inventors contemplate that the claimed subject matter might also be embodied in other ways, to include different steps or elements similar to the ones described in this document, in conjunction with other present or future technologies.

While the present technology has been described in connection with the embodiments of the various figures, it is to be understood that other similar embodiments may be used or modifications and additions may be made to the described embodiments for performing the same function of the present technology without deviating therefrom. Therefore, the present technology should not be limited to any single embodiment, but rather should be construed in breadth and scope in accordance with the appended claims. In addition, all other embodiments obtained by one of ordinary skill in the art based on embodiments described in this document are considered to be within the scope of this disclosure.

Conventional technologies for measuring blood glucose rely on infrared light. For example, a conventional glucose meter may comprise an infrared light emitting unit, an infrared light receiving unit, and a processor. The infrared light emitting unit may be configured to emit infrared light in the direction of a user's fingertip. The infrared light receiving unit may be an infrared sensor array configured to receive infrared light signals from the infrared light emitting unit, which has penetrated the user's fingertip. Infrared light may be absorbed by glucose in blood, so that the intensity of the infrared light received by the infrared light receiving unit is expected to be lower than the intensity of the infrared light originally emitted by the infrared light emitting unit. The processor, which may include an A/D converter and a CPU, can calculate the difference between the intensity of the light emitted by the emitting unit and that of the light received by the receiving unit, and based on this difference, determine the user's blood glucose level. Since infrared light is absorbed by blood glucose, there is a direct relationship between the level of blood glucose and the amount of infrared light absorption, and by calculating the difference in the intensities of the emitted and received infrared light, and comparing the calculated difference against a correlation between intensity difference and blood glucose level, which correlation may be predetermined, the level of blood glucose can be determined.

However, a drawback of the conventional technologies is that, when wide-spectrum infrared light is applied, background spectra arising from the presence of other tissue and blood components (for example, water, proteins, lipids, etc.) complicate the blood glucose measurement. In addition, other factors such as variations in the thickness of epithelia layers of skin, nails, and the like among users, and environmental factors can also make it difficult to obtain uniformly accurate measurements for different patients.

Embodiments of the present disclosure may comprise one or more processors. The processor may be central processing unit (CPU), a field-programmable gate array (FPGA), a microcontroller (MCU), a digital signal processor (DSP), an application specific integrated circuit (ASIC), or other logic devices with data processing capability and/or program execution capability. Embodiments of the present disclosure may also comprise one or more storage units. The storage unit may comprise volatile memory, non-volatile memory, or a combination thereof. More particularly, the storage unit may comprise static random access memory (SRAM), electrically erasable programmable read-only memory (EEPROM), erasable programmable read-only memory (EPROM), programmable read-only memory (PROM), read-only memory (ROM), flash, disc, CD, or the like.

In addition, in embodiments of the present disclosure, the various circuit components may be implemented as a distributed system. In that case, the various circuit components may be connected via a network, for example, a wireless fidelity (WiFi) network, a wired network, or a combination thereof. Suitable networks include a local area network (LAN), the internet, a telecommunications network, an Internet of Things-based internet and/or telecommunications network, a combination of any of the foregoing networks, and the like. If the network is a wired network, the network may be connected using twisted pair wires, coaxial cables, fiber optic cables, and the like. If the network is a wireless network, the network may be connected via 3G/4G/5G mobile communication network, Bluetooth, Zigbee, or WiFi. In embodiments of the present disclosure, when the various circuit components are integrated on a printed circuit board, the components may be connected to each other through the bus, including front side bus (FSB), QuickPath Interconnect (QPI), direct media interface (DMI), peripheral component interconnect express, general microcircuits (GM), and the like.

Embodiments of the present disclosure utilize two light emitting units to emit two lights, one of which has the characteristic of being insensitive to blood glucose. By calculating a difference between the two lights and determining the blood glucose level based on the calculated difference, the present disclosure makes it possible to reduce, and even eliminate, the effects of differences in such factors as skin pigments, temperature, and thickness on the measurements of blood glucose, which can in turn remarkably increase the accuracy and precision of such measurements. Further, the present disclosure advantageously incorporates a blood glucose detection device into a wearable device, such as a clamp assembly, which can simplify not only the configuration and design of the equipment for detecting blood glucose, but also make the operation of the equipment significantly more user-friendly.

The present disclosure provides a blood glucose detection device. The blood glucose detection device can nullify variations in blood glucose arising from changes in skin characteristics, temperature, tissue thickness, and the like, so as to significantly increase the accuracy and precision of the blood glucose measurements.

Figure 2:
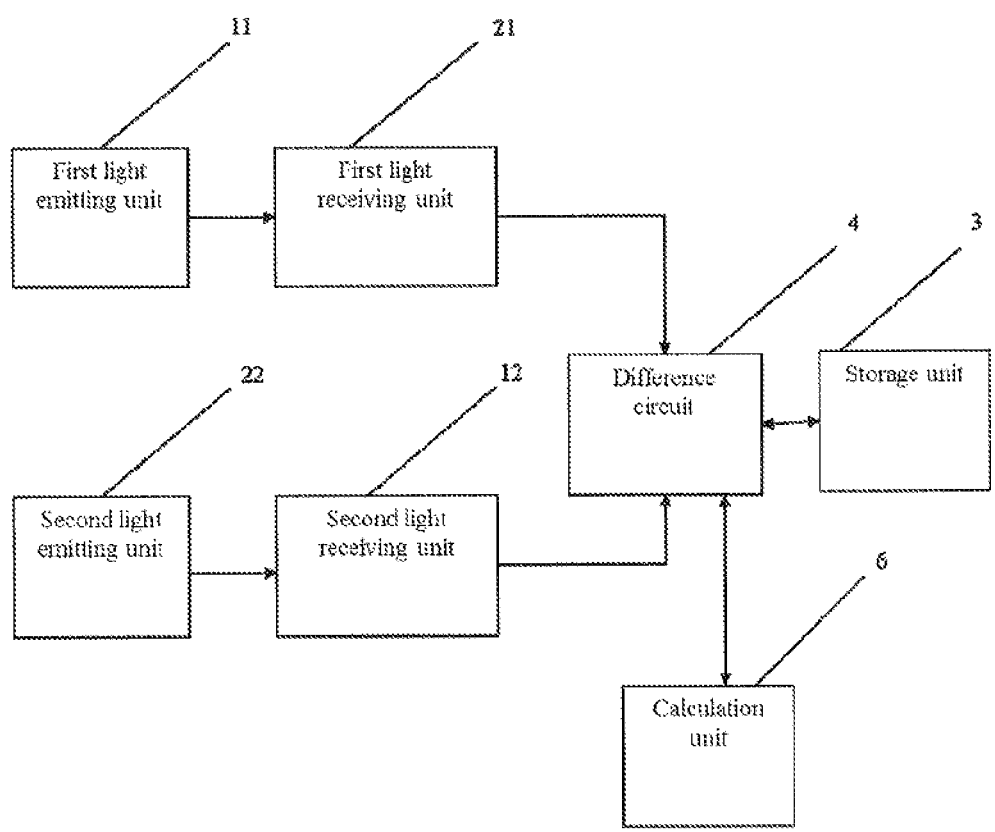
FIG. 2 shows a block diagram illustrating schematically a structure of a blood glucose detection device according to an embodiment of the present disclosure.

FIG. 1 shows a schematic diagram of a blood glucose detection device according to an embodiment of the present disclosure. FIG. 2 shows a block diagram illustrating schematically a structure of a blood glucose detection device according to an embodiment of the present disclosure.

The blood glucose detection device comprises a first light emitting unit 11, a second light emitting unit 22, a first light receiving unit 21, and a second light receiving unit 12. One of the first light emitting unit 11 and the second light emitting unit 22 is configured to emit light that is insensitive to glucose content in blood, while the other of the first light emitting unit 11 and the second light emitting unit 22 is configured to emit light that is sensitive to glucose content in blood. In embodiments of the present disclosure, sensitivity is defined as the responsiveness of a given wavelength of light to blood glucose concentration. For example, if the blood glucose concentration were increased incrementally from 0%, to 1%, 3%, 5%, 7%, and 10%, light that is sensitive to blood glucose would observe a corresponding decrease in transmittance with increasing blood glucose concentration. On the other hand, the increase in blood glucose concentration would have negligible, if any, effect on the transmittance of light that is insensitive to blood glucose. If blood glucose concentration were increased according to the above gradient, then with each incremental increase of 1% in blood glucose concentration, light that is sensitive to blood glucose would be expected in theory to decrease by 3%. In contrast, light that is insensitive to blood glucose would not be expected to change, and more particularly, even if the blood glucose concentration were increase from 1% to 10%, the transmittance of light that is insensitive to blood glucose would not be expected to vary by more than 3%. The first light emitting unit 11 and the second light emitting unit 22 may each comprise an infrared light emitting diode (IR LED).

One of the first light emitting unit 11 and the second light emitting unit 22 is configured to emit infrared light having a wavelength of 830 nm to 880 nm. Infrared light within this range is sensitive to concentration of blood glucose. An infrared light having a wavelength in this range is "glucose-linked" in that the intensity of the light as received at a light receiving unit exhibits a good correlation to the blood glucose concentration. The other of the first light emitting unit 11 and the second light emitting unit 22 is configured to emit infrared light having a wavelength of 920 nm to 950 nm. Infrared light within this range is insensitive to concentration of blood glucose. In some embodiments, one of the first light emitting unit 11 and the second light emitting unit 22 is configured to emit infrared light having a wavelength of 845 nm, and the other of the first light emitting unit 11 and the second light emitting unit 22 is configured to emit infrared light having a wavelength of 940 nm.

Generally, when light passes through a solution containing a certain concentration of an analyte, light absorbance is proportional to the wavelength of the light and the concentration of the analyte in the solution. More particularly, light absorbance can be calculated according to the equation, A=a*l*c, where a is the absorption coefficient, l is the wavelength of the light, and c is the concentration of the compound in solution. The equation is derived from the Beer-Lambert Law, A=εbc, where is the molar absorptivity (L mol$^{-1}$ cm-1), b is the optical path length (cm), and c is the concentration of the analyte in solution (mol L$^{-1}$). In addition, assuming that the intensity of the incident light is I1, and the intensity of the emitted light is I2, then according to the Beer-Lambert Law, light absorption by the solution follows the relationship, A=−log I1/I2 (logarithm with base 10). Blood glucose level can be determined based on the above functional relationships. Skin and other tissue and blood components can obstruct the transmission of light, but by basing the blood glucose level determination on the difference between lights that are emitted by two light emitting units, one of which emitted lights is insensitive to blood glucose, and that are subsequently received by two corresponding light receiving units, the present disclosure makes it possible to filter out the effects of external and environmental interferences on the resulting blood glucose level determination.

The first light receiving unit 21 and the second light receiving unit 12 may each comprise an infrared light sensor configured to receive infrared light. The first light receiving unit 21 is configured to receive light emitted by the first light emitting unit 11 after the light has passed through the blood of the user, and to generate a first signal based on the received light. The second light receiving unit 12 is configured to receive light emitted by the second light emitting unit 22 after the light has passed through the blood of the user, and to generate a second signal based on the received light. The first and second signals may be light signals representing light received by the first and second light receiving units 21, 12, respectively. The first and second signals may be electrical signals (for example, voltage signals) that are generated through photoelectric conversion of light signals received by the first and second light receiving units 21, 12, respectively.

Since light emitted by one of the first and second light emitting units 11, 22 is insensitive to blood glucose, lights received by the first light receiving unit 21 and the second light receiving unit 12 have different properties, so that the first and second signals generated by the first and second light receiving units 21, 12, respectively, are also different. A difference between the first and second signals can be calculated to generate a difference value, and the difference value can then be applied to determine the blood glucose level. In other words, embodiments of the present disclosure apply the difference between the signals generated by the first and second light receiving units 21, 12 to evaluate the blood glucose level. The use of light that is insensitive to blood glucose makes it possible to nullify interferences on measurements from external and/or environmental factors such as skin pigments, temperature changes, and tissue thickness, so as to significantly improve the accuracy of the blood glucose measurement. More particularly, by calculating the difference between the lights received at the first light receiving unit 21 and the second light receiving unit 12, and then applying that difference in the determination of the blood glucose level, it is possible to filter out background noises arising from external and/or environmental interferences and increase the accuracy and precision of the determination.

As shown in FIG. 1, a blood glucose detection device according to the present disclosure may be configured to be attached to a body part of the user, for example, onto the user's finger, wrist, or arm. In some embodiments, the blood glucose detection device is incorporated into a wearable device. In some embodiments, the wearable device is a clamp assembly. The clamp assembly may comprise a first member 1 and an opposing second member 2. There are no particular limitations on the configurations and designs of the first member 1 and the second member 2, which may be adapted by any means known to a person of ordinary skill in the art according to need. For example, as shown in FIG. 1, the first member 1 and the second member 2 may be flat, elongated plates. The first member 1 has a first clamping face 13, and the second member 2 has a second clamping face 23.

The first member 1 and the second member 2 are joined to one another by a pivotal connection (not shown in the figures), so that the first member 1 and the second member 2 are configured to articulate relative to each other. There are no particular limitations on the configurations and designs of the pivotal connection, and the first member 1 and the second member 2 may be connected by any means known to a person of ordinary skill in the art according to need. For example, as shown in FIG. 1, the first member 1 and the second member 2 are pivotally connected, so that the first and second members 1, 2 may be clamped onto a body part of the user (for example, the finger, the wrist, or some other body part).

On each of the first and second members 1, 2 are provided a light emitting unit and a light receiving unit. The first light emitting unit 11 and the first light receiving unit 21 are arranged to be directly opposite of each other. The first light receiving unit 21 is configured to receive light emitted by the first light emitting unit 11 after the light has passed through the blood of the user, and to generate a first signal based on the received light. Similarly, the second light emitting unit 22 and the second light receiving unit 12 are arranged to be directly opposite of each other. The second light receiving unit 12 is configured to receive light emitted by the second light emitting unit 22 after the light has passed through the blood of the user, and to generate a second signal based on the received light For example, as shown in FIG. 1, the first light emitting unit 11 and the second light receiving unit 12 may be provided on the first member 1, and the first light receiving unit 21 and the second light emitting unit 22 are provided on the second member 2. However, the arrangement of the light emitting units 11, 22 and the light receiving units 21, 12 is not limited to the embodiment shown in FIG. 1. The light emitting units 11, 22 and the light receiving units 21, 12 may be arranged in any suitable manner, so long as the first light emitting unit 11 and the first light receiving unit 21 are arranged to be directly opposite of each other, and the second light emitting unit 22 and the second light receiving unit 12 are arranged to be directly opposite of each other.

In the clamp assembly, each of the first light receiving unit 21 and the second light receiving unit 12 is at a distance of no more than 1 cm from a surface of the user's body part where the blood glucose level is being measured. More particularly, since the clamp assembly is configured to clamp onto the body part, the first light receiving unit 21 and the second light receiving unit 12 face opposing sides of the body part (for example, a top side and an underside). The pivotal connection joining the fit and second members 1, 2 of the clamp assembly is therefore configured to be adjustable. The pivotal connection may be adjusted to limit the opening between the first and second members 1, 2, so that a distance between each of the first light receiving unit 21 and the second light receiving unit 12 and the respective surface of the body part that they face is no more than 1 cm. In some embodiments, a hinge may be provided at the same end of the first and second members 1, 2, and a torsion spring is provided to enable one of the first and second members 1, 2 to be biased relative to the other of the first and second members 1, 2. In some embodiments, the clamp assembly may be configured to open and close in a symmetrical manner. In some embodiments, the clamp assembly may be configured as an adjustable structure, for example, by providing a snap fit or a threaded connection between the first and second members 1, 2. Maintaining the separation distance between the first and second light receiving units 21, 12 and the body part at no more than 1 cm helps facilitate effective transmission of light from the first and second light emitting units 11, 22 through the body part, which in turn optimizes the light received by the first and second light receiving units 21, 12.

As shown in FIG. 2, the blood glucose detection device may further comprise a storage unit 3, a difference circuit 4, and a calculation unit (one or more processors) 6. The storage unit 3 is configured to store a first correspondence table that comprises a plurality of difference values, a plurality of blood glucose concentrations, and a plurality of correspondence sets for each combination of corresponding difference value and blood glucose concentration.

The difference value corresponds to a difference between the first signal generated by the first light receiving unit 21 and the second signal generated by the second light receiving unit 12. The first and second signals may be light signals representing light received by the first and second light emitting units 21, 12, respectively. The first and second signals may be electrical signals (for example, voltage signals) that are generated through photoelectric conversion of light signals received by the first and second light receiving units 21, 12, respectively. In some embodiments, the storage unit 3 stores the first correspondence table.

The difference circuit 4 is connected to the first light receiving unit 21 and the second light receiving unit 12, for example, as shown in FIG. 2. The difference circuit 4 is configured to calculate a difference between the first signal generated by the first light receiving unit 21 and the second signal generated by the second light receiving unit 12, so as to generate a difference value. In some embodiments, the first signal and the second signal are electrical signals, and the difference circuit 4 is configured to calculate a difference value corresponding to a difference between the voltage values corresponding to the first signal and the second signal.

The calculation unit 6 is configured to receive the calculated difference value from the difference circuit. The calculation unit 6 is connected to the storage unit 3, and is configured to retrieve the first correspondence table, so as to correlate the calculated difference between with a corresponding blood glucose level according to the correspondence sets defined and stored in the first correspondence table. More particularly, the calculation unit 6 is configured to determine the blood glucose level by identifying a correspondence set based on the calculated difference value and determining the corresponding blood glucose concentration according to the correspondence set.

Figure 3:
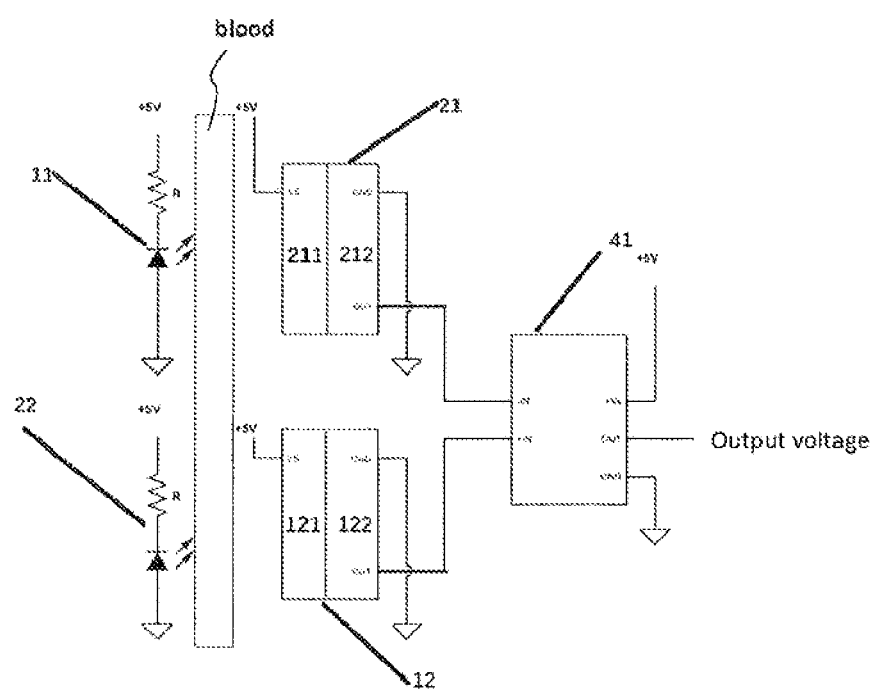
FIG. 3 shows a circuit diagram of a circuit configuration utilized in a blood glucose detection device according to an embodiment of the present disclosure.
Figure 4:
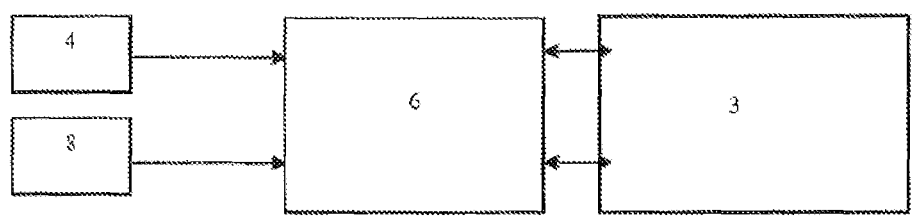
FIG. 4 shows a schematic diagram that illustrates a connection between a difference circuit, a storage unit, and a calculation unit in a blood glucose detection device according to an embodiment of the present disclosure.

FIG. 3 shows a circuit diagram of a circuit configuration utilized in a blood glucose detection device according to an embodiment of the present disclosure. FIG. 4 shows a schematic diagram that illustrates a connection between a difference circuit, a storage unit, and a calculation unit in a blood glucose detection device according to an embodiment of the present disclosure.

As shown in FIG. 3, the first light receiving unit 21 comprises a first receiving portion 211. In some embodiments, the first light receiving unit 21 may further comprise a first photoelectric conversion module 212 connected to the first receiving portion 211. The first receiving portion 211 is configured to receive light emitted from the first light emitting unit 11 after the light has passed through the blood of the user. The first photoelectric conversion module 212 is configured to convert the light received by the first receiving portion 211 into a first signal. The first receiving portion 211 may be an infrared light receiver. The first photoelectric conversion module 212 may be a photoelectric converter.

Further as shown in FIG. 3, the second light receiving unit 12 comprises a second receiving portion 121. In some embodiments, the second light receiving unit 12 may further comprise a second photoelectric conversion module 122 connected to the second receiving portion 121. The second receiving portion 121 is configured to receive light emitted from the second light emitting unit 22 after the light has passed through the blood of the user. The second photoelectric conversion module 122 is configured to convert the light received by the second receiving portion 121 into a second signal. The second receiving portion 121 may be an infrared light receiver. The second photoelectric conversion module 122 may be a photoelectric converter.

The difference circuit 4 is connected to the first light receiving unit 21 and the second light receiving unit 12, for example, as shown in FIG. 2. The difference circuit 4 is configured to receive the first signal generated by the first light receiving unit 21, which may be a first electrical signal following photoelectric conversion by the first photoelectric conversion module 212. The difference circuit 4 is also configured to receive the second signal generated by the second light receiving unit 12, which may be a second electrical signal following photoelectric conversion by the second photoelectric conversion module 122. The difference circuit 4 is configured to calculate a difference value between the first signal and the second signal.

As described above, the blood glucose detection device comprises a storage unit 3 that is configured to store a first correspondence table, which identifies a correspondence between a difference value and blood glucose concentration. The first correspondence table comprises at least one difference value, at least one blood glucose concentration, and at least one correspondence set for each combination of corresponding difference value and blood glucose concentration.

The calculation unit 6 is configured to correlate the difference value calculated by the difference circuit 4 with a corresponding blood glucose concentration according to the correspondence sets defined and stored in the first correspondence table. For example, the difference circuit 4 may calculate a difference between the voltage values corresponding to the first and second signals, and then the calculation unit 6 correlates the calculated difference value with a corresponding blood glucose level according to the correspondence sets defined and stored in the first correspondence table.

In embodiments where the blood glucose detection device is incorporated into a clamp assembly, the difference circuit 4 and the storage unit 3 may be provided directly on the clamp assembly, or may be provided as an independent unit that is detachably assembled with the clamp assembly. The difference circuit 4 and the storage unit 3 may be configured and constructed according to any suitable means known to a person of ordinary skill in the art, and are not subject to any particular limitations.

Figure 5:
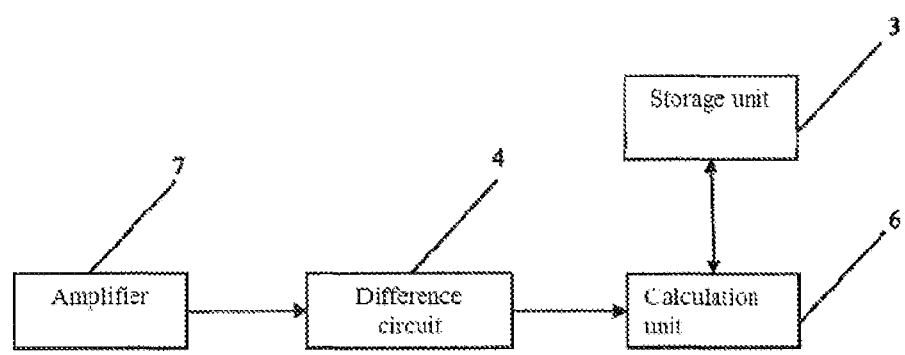
FIG. 5 shows a blood glucose detection device according to another embodiment of the present disclosure.
Figure 6:
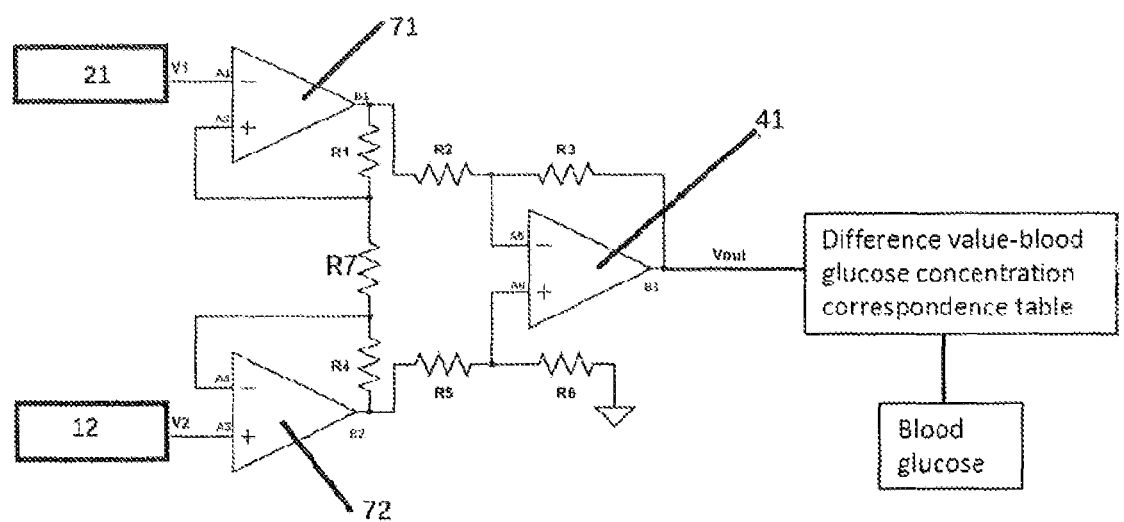
FIG. 6 shows a partial circuit diagram of a circuit configuration utilized in a blood glucose detection device according to another embodiment of the present disclosure.

The difference circuit 4 is connected to the first light receiving unit 21 via a first input, and to the second light receiving unit 12 via a second input, for example, as shown in FIG. 6. An output of the difference circuit 4 is connected to the calculation unit 6, for example, as shown in FIGS. 2, 4, and 5. The difference circuit 4 is configured to receive the first signal generated by the first light receiving unit 21 and the second signal generated by the second light receiving unit 12, and to calculate a difference value corresponding to a difference between the first signal and the second signal. The difference value is then output to the calculation unit 6.

The calculation unit 6 is connected to the storage unit 3, for example, as shown in FIGS. 4 and 5. The storage unit 3 is configured to store a first correspondence table that comprises a plurality of difference values, a plurality of blood glucose concentrations, and a plurality of correspondence sets for each combination of corresponding difference value and blood glucose concentration.

As shown in FIG. 4, the calculation unit 6 is connected to the storage unit 3, and is configured to retrieve the first correspondence table from the storage unit 3, so that the blood glucose level may be determined based on the calculated difference value between the first signal and the second signal. More particularly, the calculation unit 6 is configured to receive the calculated difference value from the difference circuit, and to determine the blood glucose level by identifying a correspondence set based on the calculated difference value and determining the corresponding blood glucose concentration according to the correspondence set.

In some embodiments, the calculation unit 6 may be configured to directly acquire from the storage unit 3 the blood glucose level corresponding to the calculated difference value, without the step of retrieving the first correspondence table. Bypassing the step of retrieving the first correspondence table may be more convenient and efficient.

In some embodiments, the blood glucose detection device may comprise an output unit connected to the calculation unit 6. The blood glucose level determined by the calculation unit 6 may then be communicated to the user through the output unit. The output unit may comprise at least one of a display unit, an audio unit, and a communication output unit. The display unit is configured to communicate the blood glucose level determination visually. The audio unit is configured to communicate the blood glucose level determination audibly. The communication output unit is configured to transmit the blood glucose level determination to other electronic devices and/or to a terminal server for storage. A user can therefore be notified of the blood glucose level determination through multiple channels, which increases convenience and improves the general user experience.

FIG. 5 shows a blood glucose detection device according to another embodiment of the present disclosure. FIG. 6 shows a partial circuit diagram of a circuit configuration utilized in a blood glucose detection device according to another embodiment of the present disclosure.

In some embodiments, the blood glucose detection device further comprises an amplifier 7, for example, as shown in FIG. 5. The amplifier 7 may comprise a first input connected to the first light receiving unit 21, and a second input connected to the second light receiving unit 12, for example, as shown in FIG. 6. The amplifier 7 is configured to receive and amplify the first signal generated by the first light receiving unit 21, to receive and amplify the second signal generated by the second light receiving unit 12, and to transmit the amplified first signal and the amplified second signal to the difference circuit 4.

In some embodiments, the amplifier 7 may comprise a first amplifier 71 and a second amplifier 72. The first amplifier 71 may be connected to the first light receiving unit 21, so as to amplify the received first signal and to transmit the amplified first signal to the difference circuit 4. The second amplifier 72 may be connected to the second light receiving unit 12, so as to amplify the received second signal and to transmit the amplified second signal to the difference circuit 4.

The amplifier 7 may be connected to the difference circuit 4. The difference circuit 4 is configured to receive the amplified first signal and the amplified second signal from the amplifier 7. The difference circuit 4 is configured to calculate a difference value between the amplified first signal and the amplified second signal. For example, the difference circuit 4 may calculate a difference between the voltage values corresponding to the amplified first signal and the amplified second signal, and then the calculation unit 6 matches the difference value with a corresponding blood glucose level according to the correspondence sets defined and stored in the first correspondence table stored in the storage unit 3.

FIG. 6 shows a partial circuit diagram of a circuit configuration utilized in a blood glucose detection device according to another embodiment of the present disclosure. As shown in FIG. 6, the amplifier 7 may further comprise a first resister R1, a second resistor R2, a fourth resistor R4, and a seventh resistor R7. The first amplifier 71 has a first input A1 connected to an output of the first light receiving unit 21. The first amplifier 71 also has a second input A2 and a first output B1 that are respectively connected to either side of the first resistor R1. The second amplifier 72 has a third input A3 connected to an output of the second light receiving unit 12. The second amplifier 72 also has a fourth input A4 and a second output B2 that are respectively connected to either side of the fourth resistor R4. The seventh resistor R7 is provided between the first resister R1 and the fourth resistor R4. The first output B1 is connected to one side of the second resistor R2, and the second output B2 is connected to one side of the fifth resistor R5. The side of each of the second resistor R2 and the fifth resistor R5 that is not connected to the first output B1 or the second output B2 is connected to an input of the difference circuit 4.

As shown in FIG. 6, the difference circuit 4 may comprise a third amplifier 41, a third resistor R3, and a sixth resistor R6. The third amplifier 41 has a fifth input A5 and a sixth input A6 that are connected to the first output B1 and second output B2, respectively, of the amplifier 7. More particularly, the fifth input A5 is connected to the side of the second resistor R2 that is not connected to the first output B1, and the sixth input A6 is connected to the side of the firth resistor R5 that is not connected to the second output B2. The difference circuit 4 may further comprise a third output B3. The third resistor R3 is provided between the fifth input A5 and the third output B3. The sixth input A6 is grounded via the sixth resistor R6.

In order for the algorithm for determining blood glucose level described above to be compatible with photoelectric conversion, the first amplifier 71 is an inverting amplifier with respect to the input voltage V1, the voltage being transmitted from the first light receiving unit 21. If the initial amplified output voltage from the first amplifier 72 is V01, then $$\frac{V01}{V1} = \frac{R1}{R7}.$$

The second amplifier 72 is a non-inverting amplifier with respect to the input voltage V2, the voltage being transmitted from the second light receiving unit 12. If the initial amplified output voltage from the second amplifier 72 is V02, then $$\frac{V02}{V2} = 1 + \frac{R4}{R7}.$$

The amplified first signal that originates from the first light receiving unit 21 is V1, and the amplified second signal that originates from the second light receiving unit 12 is V1. R1 may be set to be the same as R4, R2 the same as R5, and R3 the same as R6. The voltage signals passing through the first amplifier 71 and the second amplifier 72 have the same amplitude and the same phase. The third amplifier 41 is a differential amplifier configured to amplify the difference between V01 and V02, and more particularly, $$V01 - V02 = (V1 - V2) \times \left(1 + 2\frac{R1}{R7}\right)$$

and the output voltage from the third amplifier 41 is $$V_{out} = (V01 - V02) \times \frac{R3}{R2}.$$

Therefore, the amplification of $V_{out}$ can be adjusted so that $$V_{out} = \left(1 + 2\frac{R1}{R7}\right) \times \frac{R3}{R2}.$$

The present disclosure thus makes it possible to adjust the amplification factor according to the different settings on the resistors, which can in turn improve the versatility and usefulness of the blood glucose detection device.

The calculation unit 6 may be configured to receive the output voltage $V_{out}$ from the third amplifier 41, and to correlate the difference value (representing the difference in voltage signals) with the corresponding blood glucose level according to the correspondence sets defined in the first correspondence table stored in the storage unit 3.

In some embodiments of the present disclosure, the blood glucose detection device does not include an amplifier. The first correspondence table for embodiments without an amplifier is different from the first correspondence table for embodiments with an amplifier. More particularly, the first correspondence tables may have different correspondence sets for combinations of corresponding difference values representing differences in voltage signals and blood glucose concentrations. However, the first correspondence tables may be reconciled by applying the appropriate amplification factors.

Embodiments of the present disclosure apply the difference between the signals generated by the first and second light receiving units to evaluate the blood glucose level. The use of light that is insensitive to blood glucose makes it possible to nullify obstructions to blood glucose measurements by external and/or environment factors such as skin pigments, temperature changes, and tissue thickness, so as to significantly improve the accuracy of the blood glucose measurement. More particularly, by calculating the difference between the lights received at the first and second light receiving units, and then factoring that difference into the blood glucose level determination, it is possible to filter out noises from external and/or environment interferences and increase the accuracy and precision of the determination.

In some embodiments, the first light receiving unit 21 and the second light receiving unit 12 may each be provided with a light filter 5, for example, as shown in FIG. 1. The first light filter 5a provided on the first light receiving unit 21 is configured to filter out light that is not emitted by the first light emitting unit 11. The second light filter 5b provided on the second light receiving unit 12 is configured to filter out light that is not emitted by the second light emitting unit 22. In other words, the first filter 5a is configured to transmit only light emitted by the first light emitting unit 11, and the second filter 5b is configured to transmit only light emitted by the second light emitting unit 22. This configuration ensures that the first and second light receiving units 21, 12 receive only lights emitted by the corresponding light emitting unit, so as to reduce, or even eliminate, interferences from ambient light or other light sources. This can in turn further improve the accuracy of the blood glucose measurement.

In some embodiments, the blood glucose detection device is further configured to determine a body temperature and to determine a correction value to be applied to the blood glucose level determination, by identifying a correspondence set based on the measured body temperature and determining the corresponding body temperature-dependent deviation in blood glucose concentration. In some embodiments, the blood glucose detection device may be further configured to measure the body temperature of the user and to correct the blood glucose level determination obtained by the calculation unit 6 based on the measured body temperature.

The effect of temperature on the absorbance of light depends on the physical nature of the light, rather than on technical errors in measurement. Consequently, temperature-related variations in blood glucose measurement are more difficult to filter out using the algorithms described above. To address the problems of body temperature-dependent fluctuations in blood glucose measurement, the blood glucose detection device according to the present disclosure may be further configured to perform correction of the blood glucose level determination based on the measured body temperature, for example, by measuring the body temperature of the user and correcting the blood glucose level determination obtained by the calculation unit 6 in accordance with the measured body temperature.

As shown in FIG. 4, a blood glucose detection device according to the present disclosure may comprise a temperature sensor 8 connected to the calculation unit 6, which is in turn connected to the storage unit 3. The temperature sensor 8 is configured to measure the body temperature of the user.

In embodiments where the blood glucose detection device is incorporated in a clamp assembly, the temperature sensor 8 may be provided on either the first member 1 or the second member 2 of the clamp assembly. Such a configuration facilitates the gathering of the user's body temperature information. In some embodiments, the temperature sensor 8 is provided on the clamping surface 13 of the first member 1 or the clamping surface 23 of the second member 2.

The storage unit 3 is configured to store a second correspondence table that comprises a plurality of body temperature values, a plurality of predetermined body temperature-dependent deviations in blood glucose concentration, and a plurality of correspondence sets for each combination of corresponding body temperature value and body temperature-dependent deviation in blood glucose concentration.

The calculation unit 6 is configured to apply a correction value to the blood glucose level determination based on the second correspondence table. More particularly, the calculation unit 6 is configured to determine a correction value to be applied to the blood glucose level determination based on the measured body temperature value and the corresponding deviation in blood glucose level as defined in the second correspondence table. The calculation unit 6 is configured to apply the correction value to the blood glucose level determination to obtain a corrected blood glucose level. The features of the present disclosure thus advantageously eliminate body temperature-dependent variations from the blood glucose level measurement.

The storage unit 3 may be configured as a cloud-based storage unit or a local memory, depending on need. The storage unit 3 may comprise volatile memory, non-volatile memory, or a combination thereof. More particularly, the storage unit may comprise static random access memory (SRAM), electrically erasable programmable read-only memory (EEPROM), erasable programmable read-only memory (EPROM), programmable read-only memory (PROM), read-only memory (ROM), flash, disc, CD, or the like.

Embodiments of the present disclosure utilize two light emitting units to emit two lights, one of which has the property of being insensitive to blood glucose. By factoring a calculated difference between the two lights into the blood glucose level determination, the blood glucose detection device according to the present disclosure makes it possible to minimize variations in blood glucose measurements due to differences in such external and/or environmental factors as skin pigments, temperature, and tissue thickness, so as to remarkably increase the accuracy and precision of such measurements. Further, embodiments of the present disclosure advantageously incorporate the blood glucose detection device in a clamp assembly, which can simplify not only the configuration and design of the equipment for detecting blood glucose, but also make the equipment significantly more user-friendly.

Figure 7:
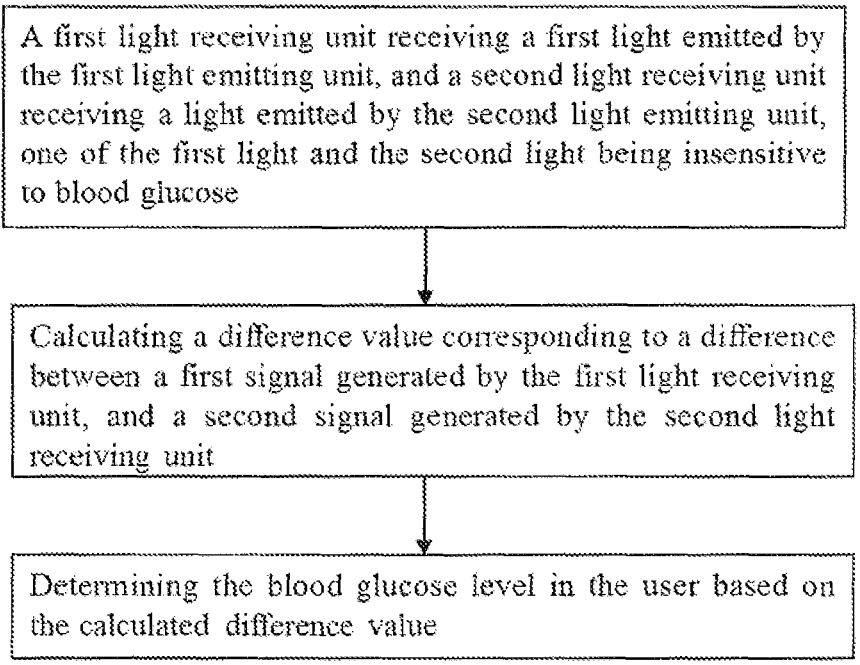
FIG. 7 shows a flow chart illustrating a method of measuring blood glucose according to an embodiment of the present disclosure.

The present disclosure also provides a method of detecting blood glucose. The method of detecting blood glucose may be executed by a blood glucose detection device as described above. FIG. 7 shows a flow chart illustrating a method of detecting blood glucose according to an embodiment of the present disclosure.

In a first step, a first light receiving unit receives a first light emitted by a first light emitting unit, and a second light receiving unit receives a second light emitted by a second light emitting unit, one of the first light and second light being insensitive to blood glucose.

More particularly, the first light receiving unit generates a first signal based on the first light, and the second light receiving unit generates a second signal based on the second light. As shown in FIGS. 1 and 2, the blood glucose detection device according to the present disclosure comprises a first light emitting unit 11, a second light emitting unit 22, a first light receiving unit 21, and a second light receiving unit 12. One of the first light emitting unit 11 and the second light emitting unit 22 is configured to emit light that is insensitive to blood glucose content, while the other of the first light emitting unit 11 and the second light emitting unit 22 is configured to emit light that is sensitive to blood glucose. More particularly, one of the first light emitting unit 11 and the second light emitting unit 22 is configured to emit infrared light having a wavelength of 830 nm to 880 nm. Infrared light within this range is sensitive to blood glucose. The other of the first light emitting unit 11 and the second light emitting unit 22 is configured to emit infrared light having a wavelength of 920 am to 950 nm. Infrared light within this range is insensitive to blood glucose. In some embodiments, one of the first light emitting unit 1 and the second light emitting unit 22 is configured to emit infrared light having a wavelength of 845 nm, and the other of the first light emitting unit 1 and the second light emitting unit 22 is configured to emit infrared light having a wavelength of 940 nt.

In a second step, a difference value corresponding to a difference between the first signal and the second signal is calculated, and a blood glucose level is determined based on the calculated difference value. More particularly, based on the calculated difference value, a first correspondence table stored in a storage unit is searched for an appropriate correspondence set of corresponding difference value and blood glucose concentration.

As shown in FIG. 2, the blood glucose detection device according to the present disclosure further comprises a storage unit 3, a difference circuit 4, and a calculation unit 6. The storage unit 3 is configured to store the first correspondence table. The first correspondence table comprises at least one difference value, at least one blood glucose concentration, and at least one correspondence set for each combination of corresponding difference value and blood glucose concentration. The difference value corresponds to a difference between the first signal generated by the first light receiving unit 21 and the second signal generated by the second light receiving unit 12.

The difference circuit 4 is configured to calculate a difference between the first signal generated by the first light receiving unit 21 and the second signal generated by the second light receiving unit 12, so as to generate the difference value.

The calculation unit 6 is configured to identify a correspondence set in the first correspondence table that contains the calculated difference value, and to acquire from the identified correspondence set the blood glucose concentration corresponding to the calculated difference value, so as to determine the blood glucose level of the user.

Generally, when light passes through a solution containing a certain concentration of an analyte, light absorbance is proportional to the wavelength of the light and the concentration of the analyte in the solution. More particularly, light absorbance can be calculated according to the equation, $A=a*l*c$, where a is the absorption coefficient, l is the wavelength of the light, and c is the concentration of the analyte in solution. The equation is derived from the Beer-Lambert Law, $A=\varepsilon bc$, where $\varepsilon$ is the molar absorptivity (L $mol^{-1}$ cm-1), b is the optical path length (cm), and c is the concentration of the analyte in solution (mol $L^{-1}$). In addition, assuming that the intensity of the incident light is I1, and the intensity of the emitted light is I2, then according to the Beer-Lambert Law, light absorption by the solution follows the relationship, $A=-\log I1/I2$ (logarithm with base 10). Blood glucose level can be determined based on the above functional relationships. Skin and other tissue and blood components can obstruct the transmission of light, but by basing the blood glucose level determination on the difference between lights that are emitted by two light emitting units, one of which emitted lights is insensitive to blood glucose, and that are subsequently received by two corresponding light receiving units, the present disclosure makes it possible to filter out the effects of external and environmental interferences on the resulting blood glucose level determination.

In some embodiments, the method of detecting blood glucose level may further comprise, before the second step, a step of amplifying the first signal generated by the first light receiving unit and the second signal generated by the second light receiving unit. In such embodiments, the step of calculating a difference value comprises calculating a difference between the amplified first signal and the amplified second signal.

More particularly, in some embodiments, the blood glucose detection device may further comprise an amplifier 7, which is connected to the difference circuit 4. The amplifier 7 comprises a first input connected to the first light receiving unit 21, and a second input connected to the second light receiving unit 12, for example, as shown in FIG. 6. The amplifier 7 is configured to receive and amplify the first signal generated by the first light receiving unit 21, to receive and amplify the second signal generated by the second light receiving unit 12, and to transmit the amplified first signal and the amplified second signal to the difference circuit 4.

In some embodiments, the amplifier 7 may comprise a first amplifier 71 and a second amplifier 72. The first amplifier 71 may be connected to the first light receiving unit 21, so as to amplify the received first signal and to transmit the amplified first signal to the difference circuit 4. The second amplifier 72 may be connected to the second light receiving unit 12, so as to amplify the received second signal and to transmit the amplified second signal to the difference circuit 4.

The difference circuit 4 is configured to receive the amplified first signal and the amplified second signal from the amplifier 7. The difference circuit 4 is configured to calculate a difference value corresponding to a difference between the amplified first signal and the amplified second signal. The calculation unit 6 is then configured to match the calculated difference value with a corresponding blood glucose concentration according to the correspondence sets defined and stored in the first correspondence table stored in the storage unit 3. The first correspondence table for a blood glucose detection device without an amplifier is different from the first correspondence table for a blood glucose detection device with an amplifier. The first correspondence tables may have different correspondence sets for combinations of corresponding difference values and blood glucose concentrations. However, the first correspondence tables may be reconciled by applying the appropriate amplification factors.

In some embodiments, the method for detecting blood glucose may further comprise measuring a body temperature of the body, and correcting the blood glucose level determination obtained by the calculation unit, based on the measured body temperature.

More particularly, the blood glucose detection device may be further configured to measure the body temperature of the user and to correct the blood glucose level determination obtained by the calculation unit 6 based on the measured body temperature. As shown in FIG. 4, the blood glucose detection device may comprise a temperature sensor 8 connected to the calculation unit 6, which is in turn connected to the storage unit 3. The temperature sensor 8 is configured to measure the body temperature of the user.

The storage unit 3 is configured to store a second correspondence table that identifies a correspondence between temperature and a deviation in blood glucose concentration. The second correspondence table comprises at least one body temperature value, at least one predetermined body temperature-dependent deviation in blood glucose concentration, and at least one correspondence set for each combination of corresponding body temperature value and deviation in blood glucose concentration.

The calculation unit 6 is configured to apply a correction value to the blood glucose level determination based on the second correspondence table.

More particularly, the calculation unit 6 is configured to determine a correction value to be applied to the blood glucose level determination based on the measured body temperature value and the corresponding deviation in blood glucose level as defined in the second correspondence table. The calculation unit 6 is configured to apply the correction value to the blood glucose level determination to obtain a corrected blood glucose level.

A person of ordinary skill in the art readily understands that all or part of the steps of the blood glucose detection method of the present disclosure may be implemented by hardware, or by programming the applicable hardware with the proper software programs. The software programs may be stored in the storage unit described above or a separate computer-readable storage medium that may be a read-only memory, a magnetic disk, or an optical disk.

It should be appreciated that changes could be made to the embodiments described above without departing from the inventive concepts thereof. It should be understood, therefore, that this invention is not limited to the particular embodiments disclosed, but it is intended to cover modifications within the spirit and scope of the present invention as defined by the appended claims.

What is claimed is:

1. A device for determining a blood glucose level, comprising:
   a first light emitting unit configured to emit a first light;
   a second light emitting unit configured to emit a second light, wherein one of the first light and the second light is configured to be insensitive to glucose content in blood;
   a first light receiving unit configured to detect the first light and generate a first voltage value based on the first light;
   a second light receiving unit configured to detect the second light and generate a second voltage value based on the second light;
   a difference circuit configured to receive the first voltage value and the second voltage value from the first light receiving unit and the second light receiving unit, respectively, and to calculate a difference value corresponding to a difference between the first voltage value and the second voltage value; and
   a calculation unit configured to receive the calculated difference value from the difference circuit, and to determine the blood glucose level by correlating the calculated difference value to a corresponding blood glucose concentration,
   wherein the device further includes a first member and a second member, the first light emitting unit and the second light receiving unit are attached to the first member, and the second light emitting unit and the first light receiving unit are attached to the second member; and
   the first light propagates along a first light direction from the first member to the second member, the second light propagates along a second light direction from the second member to the first member, and the first light direction is opposite to the second emitting direction.

2. The device according to claim 1, wherein:
   the one of the first light and second light that is configured to be insensitive to glucose content in blood has a first wavelength in the range of 920 nm to 950 nm; and
   the other of the first light and second light has a second wavelength in the range of 830 nm to 880 nm.

3. The device according to claim 1, further comprising a storage unit configured to store a first correspondence table,
   wherein the first correspondence table comprises a plurality of difference values, a plurality of blood glucose concentrations, and a plurality of correspondence sets for each combination of corresponding difference value and blood glucose concentration.

4. The device according to claim 3, wherein the calculation unit configured to determine the blood glucose level by identifying a correspondence set based on the calculated difference value and determining the corresponding blood glucose concentration according to the correspondence set.

5. The device according to claim 4,
   wherein the storage unit is further configured to store a second correspondence table, and
   wherein the second correspondence table comprises a plurality of body temperature values, a plurality of predetermined body temperature-dependent deviations in blood glucose concentration, and a plurality of correspondence sets for each combination of corresponding body temperature value and body temperature-dependent deviation in blood glucose concentration.

6. The device according to claim 5, wherein the device is further configured to determine a body temperature and to determine a correction value to be applied to the blood glucose level determination, by identifying a correspondence set based on the measured body temperature and determining the corresponding body temperature-dependent deviation in blood glucose concentration.

7. The device according to claim 1, further comprising an amplifier connected to the difference circuit, and configured to amplify the first voltage value and the second voltage value,
   wherein the amplifier comprises a first amplifier configured to receive and amplify the first voltage value and a second amplifier configured to receive and amplify the second voltage value.

8. The device according to claim 7, wherein the difference circuit comprises a third amplifier configured to amplify the difference between the first voltage value and the second voltage value.

9. The device according to claim 8, wherein:
   the first amplifier is an inverting amplifier,
   the second amplifier is a non-inverting amplifier, and
   the third amplifier is a differential amplifier.

10. A wearable device for determining a blood glucose level, comprising:
    the device according to claim 1.

11. The wearable device according to claim 10, wherein:
    the wearable device is a clamp assembly comprising the first member and the second member joined to one another by a pivotal connection.

12. A method of determining a blood glucose level, comprising:
- receiving a first light emitted by a first light emitting unit;
- receiving a second light emitted by a second light emitting unit, wherein one of the first light and the second light is configured to be insensitive to glucose content in blood;
- generating a first voltage value based on the received first light, and generating a second voltage value based on the received second light;
- calculating a difference value directly corresponding to a difference between the first voltage value and the second voltage value; and
- determining the blood glucose level by correlating the calculated difference value to a corresponding blood glucose concentration.

13. The method according to claim 12,
wherein the first voltage value is an amplified first voltage value and the second voltage value is an amplified second first voltage value.

14. The method according to claim 13, further comprising:
- measuring a body temperature;
- calculating a correction value corresponding to a deviation in the blood glucose level determination in accordance with the measured body temperature; and
- applying the correction value to the blood glucose level determination.

15. The method according to claim 12, further comprising:
- emitting the first light from the first light emitting unit along a first light direction;
- emitting the second light from the second light emitting unit along a second light direction;
- wherein the first light direction is opposite to the second light direction.

* * * * *